US010112143B2

(12) United States Patent
Kumar et al.

(10) Patent No.: US 10,112,143 B2
(45) Date of Patent: Oct. 30, 2018

(54) GRAFTED POLYMER NANOCOMPOSITE MATERIALS, SYSTEMS, AND METHODS

(71) Applicants: The Trustees of Columbia University in the City of New York, New York, NY (US); University of South Carolina, Columbia, SC (US)

(72) Inventors: Sanat K. Kumar, New York, NY (US); Christopher James Durning, New York, NY (US); Eileen Buenning, New York, NY (US); Connor Bilchak, Bronx, NY (US); Brian C. Benicewicz, Columbia, SC (US)

(73) Assignees: The Trustees of Columbia University in the City of New York, New York, NY (US); University of South Carolina, Columbia, SC (US)

( * ) Notice: Subject to any disclaimer, the term of this patent is extended or adjusted under 35 U.S.C. 154(b) by 0 days.

(21) Appl. No.: 14/878,115

(22) Filed: Oct. 8, 2015

(65) Prior Publication Data

US 2016/0101386 A1 Apr. 14, 2016

Related U.S. Application Data

(60) Provisional application No. 62/061,964, filed on Oct. 9, 2014.

(51) Int. Cl.
*B01D 53/00* (2006.01)
*B01D 53/22* (2006.01)
(Continued)

(52) U.S. Cl.
CPC ........ *B01D 53/228* (2013.01); *B01D 69/02* (2013.01); *B01D 69/148* (2013.01); *C10L 3/103* (2013.01);
(Continued)

(58) Field of Classification Search
None
See application file for complete search history.

(56) References Cited

U.S. PATENT DOCUMENTS 5,256,295 A * 10/1993 Baker ................. B01D 53/229
210/321.6
8,552,108 B2 * 10/2013 Kawakami .......... B01D 53/228
524/588
(Continued)

FOREIGN PATENT DOCUMENTS

WO WO 02/28912 A2 4/2002
WO WO 2005/034205 A2 4/2005
(Continued)

OTHER PUBLICATIONS

Takahashi, Polymer, 47 (2006) p. 7519-7534.*
(Continued)

*Primary Examiner* — Robert C Boyle
(74) *Attorney, Agent, or Firm* — Baker & Hostetler LLP

(57) ABSTRACT

Provided are methods of separating one or more components from a fluid by using membranes and other materials comprising polymer graft nanoparticles arranged in a lattice structure. The disclosed compositions exhibit an increase in selectivity between two penetrants that is greater than the neat polymer selectivity for those penetrants. The compositions also exhibit an increase in selectivity between two penetrants with increasing permeability. Also provided are systems for effecting such separations, systems for agent detection, and additional methods for constructing separation components.

5 Claims, 13 Drawing Sheets

(51) Int. Cl.
*C10L 3/10* (2006.01)
*B01D 69/14* (2006.01)
*G01N 21/78* (2006.01)
*G01N 33/00* (2006.01)
*B01D 69/02* (2006.01)
*B01D 71/02* (2006.01)
*B01D 71/78* (2006.01)

(52) U.S. Cl.
CPC ............ *C10L 3/104* (2013.01); *G01N 21/78* (2013.01); *G01N 33/0009* (2013.01); *B01D 71/022* (2013.01); *B01D 71/024* (2013.01); *B01D 71/027* (2013.01); *B01D 71/78* (2013.01); *B01D 2053/221* (2013.01); *B01D 2256/24* (2013.01); *B01D 2257/304* (2013.01); *B01D 2257/504* (2013.01); *B01D 2325/20* (2013.01); *C10L 2290/548* (2013.01); *G01N 2201/068* (2013.01); *Y02C 10/10* (2013.01)

(56) References Cited

U.S. PATENT DOCUMENTS

| | | | |
|---|---|---|---|
| 2009/0092803 A1* | 4/2009 | Bita | C08F 297/02 428/209 |
| 2010/0087603 A1 | 4/2010 | Brittain et al. | |
| 2010/0303874 A1* | 12/2010 | Akcora | B82Y 30/00 424/401 |
| 2013/0041112 A1 | 2/2013 | Benicewicz et al. | |
| 2014/0128503 A1 | 5/2014 | Karl et al. | |

FOREIGN PATENT DOCUMENTS

| | | |
|---|---|---|
| WO | WO 2008/080908 A2 | 7/2008 |
| WO | WO 2010/049535 A1 | 5/2010 |
| WO | WO 2014/073960 A1 | 5/2014 |

OTHER PUBLICATIONS

Lattice Definition from Merriam Webster (2017) found at https://www.merriam-webster.com/dictionary/lattice. (Year: 2017).*
Bohaty, Langmuir, 2009, 25, p. 3096-3101 (Year: 2009).*
Koh, Journal of Membrane Science, 339 (2009) (Year: 2009).*
Kumar, Macromolecules, 2013, 46, p. 3199-3214 (Year: 2013).*
Wu, J. Am. Chem. Soc., 2008, 130, p. 3516-3520 (Year: 2008).*
Benicewicz, et al., "A Versatile Method to Prepare RAFT Agent Anchored Substrates and the Preparation of PMMA Grafted Nanoparticles", Macromolecules, Apr. 2006, 39, 3175-3183.
Koemer, et al., "Non-Isotropic Self-Organization of Single-Component Hairy Nanoparticle Assemblies", ACS Macro Letters 2013, 2, 670-676.
Freeman, et al., "Hydrogen Purification Using Advanced Polymeric Membranes" DOE Report Hydrogen Program, 2007, 994-996.
Fujita, et al., "Concentration and Temperature Dependence of Diffusion Coeffients for Systems Polymethyl Acrylate and n-Alkyl Acetates", Transactions of the Faraday Society, Jan. 1960, vol. 56, 424-437.
Harton, et al., "Immobilized Polymer Layers on Spherical Nanoparticles", Macromolecules, Mar. 2010, 43(7), 3415-3421.
Janes, et al., "Interval Sorption of Alkyl Acetates and Bensenes in Poly(methyl acrylate)", Industrial & Engineering Chemical Research, Sep. 19, 2012, 8765-8773.
Li, et al., Industrial & Engineering Chemistry Research 2010, "Rubbery Polymer—Inorganic Nanocomposite Membranes: Free Volume Characteristics on Separation Property", Ind. Eng. Chem. Res., 2010, 49(24), 12444-12451.
Matteucci, et al. "Nanoparticle Filled Rubbery Polymer Membranes for CO2 Sequestration", http://www3.aiche.org/proceedings/Abstract.aspx?PaperID=29097, accessed Dec. 7, 2015.
Takahashi, et al., "Gas Permeation in Poly(Ether Imide) Nanocomposite Membranes Based on Surface-Treated Silica. Part 1: Without Chemical Coupling to Matrix", Polymer, 47(21), 7519-7534, published 2006.

* cited by examiner

GRAFTED POLYMER NANOCOMPOSITE MATERIALS, SYSTEMS, AND METHODS

RELATED APPLICATION

The present application claims priority to U.S. Patent Application Ser. No. 62/061,964, "Transport Channels in Grafted Polymer Nanocomposite Membranes" (filed Oct. 9, 2014), the entirety of which application is incorporated herein by reference for any and all purposes.

TECHNICAL FIELD

The present disclosure relates to the field of polymer-grafted nanoparticles and to the field of fluid separations.

BACKGROUND

Given the U.S. Energy Information Administration's projection that shale gas consumption will increase by over 450% by 2025, the drawbacks of existing separation methods will become only more harmful. Existing technologies for gas separations (i.e., fractional distillation) are cost- and energy-intensive and pose risks to the environment. Additionally, distillation units must often be tailor-designed for specific feedstocks to operate efficiently, but because gas composition can vary dramatically based on the geographical location of the deposit, large-scale implementation of distillation can be difficult. Removal of the acid gas impurities present in crude natural gas—such as carbon dioxide and hydrogen sulfide—remains a further challenge, as these impurities cause equipment corrosion and pose a human health risk.

Membrane separations have found increased use in industrial applications as an alternative approach where conventional separation techniques fall short. Membrane units also possess the ability to accomplish separations traditionally difficult for distillation, such as breaking azeotropes. But there is a well-known tradeoff between the permeability and selectivity of membranes due to their sieving effects, which tradeoff is shown by the well-known "Robeson plot." Advances in materials design have led to an upward shift in this upper bound, but there is still a long-felt need in the art for improved separation materials and methods, particularly for technologies that address the tradeoff between permeability and selectivity.

Current polymeric membranes for liquid and vapor separations suffer from various limitations. First, such membranes have a relatively short lifespan before they require replacement or reprocessing, after which reprocessing their effectiveness may be reduced. Second, existing membranes vary in quality and performance, meaning that two membranes produced in a similar way may not exhibit similar performance in the field. Accordingly, there is a long-felt need in the art for improved fluid separation materials and related methods.

SUMMARY

Provided here are, inter alia, membranes with self-assembled polymer grafted nanoparticles, which membranes are easily adapted for a variety of applications by tuning their transport properties. These materials have applicability to natural gas production as well as separations technology across multiple industries.

In one aspect, the present disclosure first provides methods. These methods include contacting a fluid having at least two components to a membrane under such conditions such that one of the at least two components of the fluid is preferentially passed through the membrane, the membrane comprising a plurality of graft nanoparticles, a graft nanoparticle comprising a nanoparticle (a) having an average cross-sectional dimension in the range of from about 1 nm to about 50 nm and (b) having a population of polymer chains attached thereto, the plurality of graft nanoparticles being arranged in a lattice structure.

In another aspect, the present disclosure provides systems. The systems suitably include a chamber having an inlet, the inlet in fluid communication with a first membrane, the first membrane comprising a plurality of graft nanoparticles, a graft nanoparticle comprising a nanoparticle (a) having an average cross-sectional dimension in the range of from about 1 nm to about 50 nm and (b) having a population of polymer chains attached thereto, and the plurality of graft nanoparticles being arranged in a lattice structure.

The present disclosure also provides additional methods. These methods include assembling a plurality of graft nanoparticles into a structure, a graft nanoparticle comprising a nanoparticle (a) having an average cross-sectional dimension in the range of from about 1 nm to about 50 nm and (b) having a population of polymer chains attached thereto, the plurality of graft nanoparticles being arranged in a lattice structure, and selecting one or more of the nanoparticles, the polymer chains, a solvent, or a moiety attached to the polymer chains so as to construct a membrane that preferentially passes therethrough one or more pre-selected components of a fluid comprising the one or more pre-selected components and at least one additional component.

Further provided are compositions, the compositions comprising a plurality of graft nanoparticles, a graft nanoparticle comprising a nanoparticle (a) having an average cross-sectional sectional dimension in the range of from about 1 nm to about 50 nm and (b) having a population of polymer chains attached thereto.

Additionally disclosed are sensing devices, comprising: a first assembly of a plurality of graft nanoparticles, a graft nanoparticle comprising a nanoparticle (a) having an average cross-sectional dimension in the range of from about 1 nm to about 50 nm and (b) having a population of polymer chains attached thereto, and the plurality of graft nanoparticles being arranged in a lattice structure; and a detector configured to detect a physical change in the assembly related to the assembly's exposure to an agent.

BRIEF DESCRIPTION OF THE DRAWINGS

The summary, as well as the following detailed description, is further understood when read in conjunction with the appended drawings. For the purpose of illustrating the disclosed subject matter, there are shown in the drawings exemplary embodiments of the disclosed subject matter; however, the disclosed subject matter is not limited to the specific methods, compositions, and devices disclosed. In addition, the drawings are not necessarily drawn to scale. In the drawings:

As shown in FIG. 11, neat polymer favors the larger (butyl vs. ethyl) penetrant (solubility-limited), but the grafted material favors diffusion of the smaller penetrant, as diffusion of butyl is less than the diffusion of ethyl based on molecular size. But as shown in FIG. 10, a user may control selectivity by changing graft density as shown; structuring increased $P_{EtAC}$ (diffusion-limited at higher graft density).

DETAILED DESCRIPTION OF ILLUSTRATIVE EMBODIMENTS

The present disclosure can be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular embodiments by way of example only and is not intended to be limiting of the claimed subject matter. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the disclosed subject matter which are, for clarity, described herein in the context of separate embodiments, can also be provided in combination in a single embodiment. Conversely, various features of the disclosed subject matter that are, for brevity, described in the context of a single embodiment, can also be provided separately or in any subcombination. Further, reference to values stated in ranges includes each and every value within that range. Any documents cited herein are incorporated herein by reference in their entireties for any and all purposes.

Figure 1:
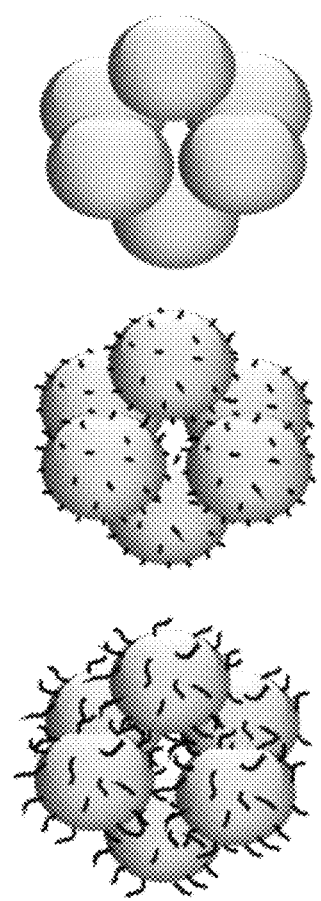
FIG. 1 provides a non-limiting schematic of hypothesized void space and tunnels due to varying chain length on polymer grafted nanoparticles—(upper image) shows bare particles, (middle image) shows particles with short grafted chains and a moderate sized "channel," and (lower image) shows particles with longer grafted chains; it is seen that the size of the "channel" decreases in size as chains begin to fill interstitial space.
Figure 2:
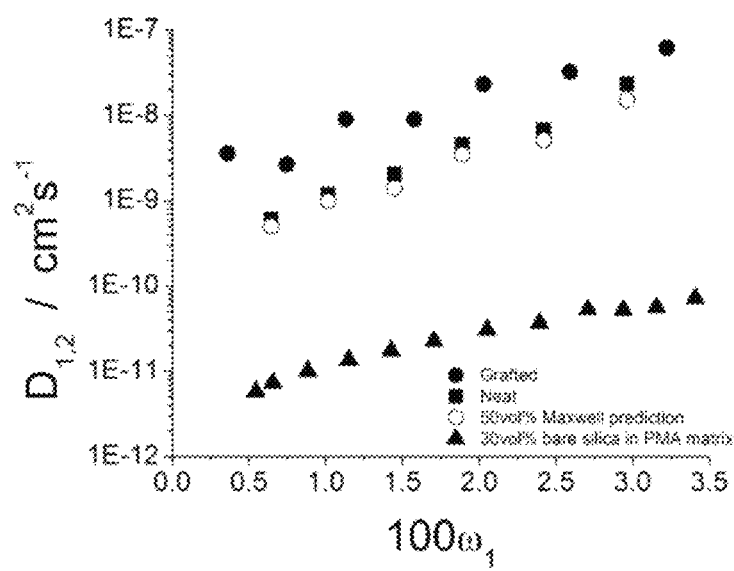
FIG. 2 shows illustrative average diffusivity values versus ethyl acetate concentration in the film for a neat PMA film and for an illustrative film comprising grafted particles. Neat PMA diffusivities are in agreement with data by Fujita et al. (Sep. 7, 1959, Transactions of the Faraday Society, Vol. 56, pp. 424-437). As seen—and as contrary to conventional composite theory—grafted particle diffusivities are larger than those of neat PMA films. The neat film in FIG. 2 is a 130k PMA melt, with no additional materials added. The grafted film in FIG. 2 is 72k PMA grafted to 14 nm silica at a grafting density of about 0.1 chains/nm$^2$.
Figure 3:
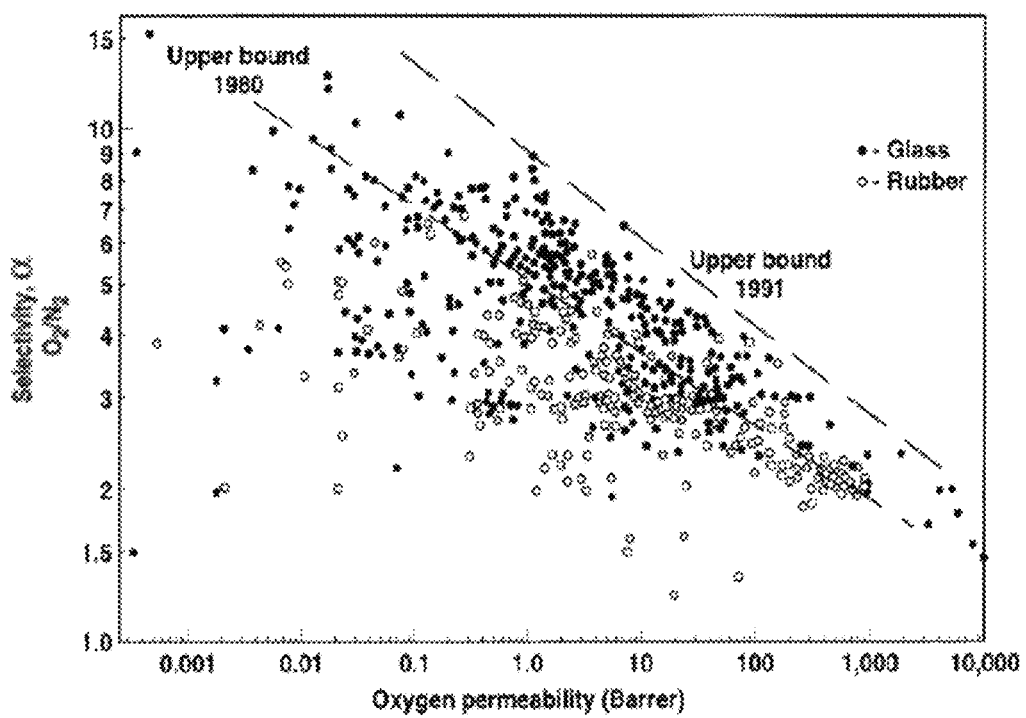
FIG. 3 provides an exemplary Robeson plot in which is seen an increase, over time, in the upper bound of permeability vs. selectivity.
Figure 4:
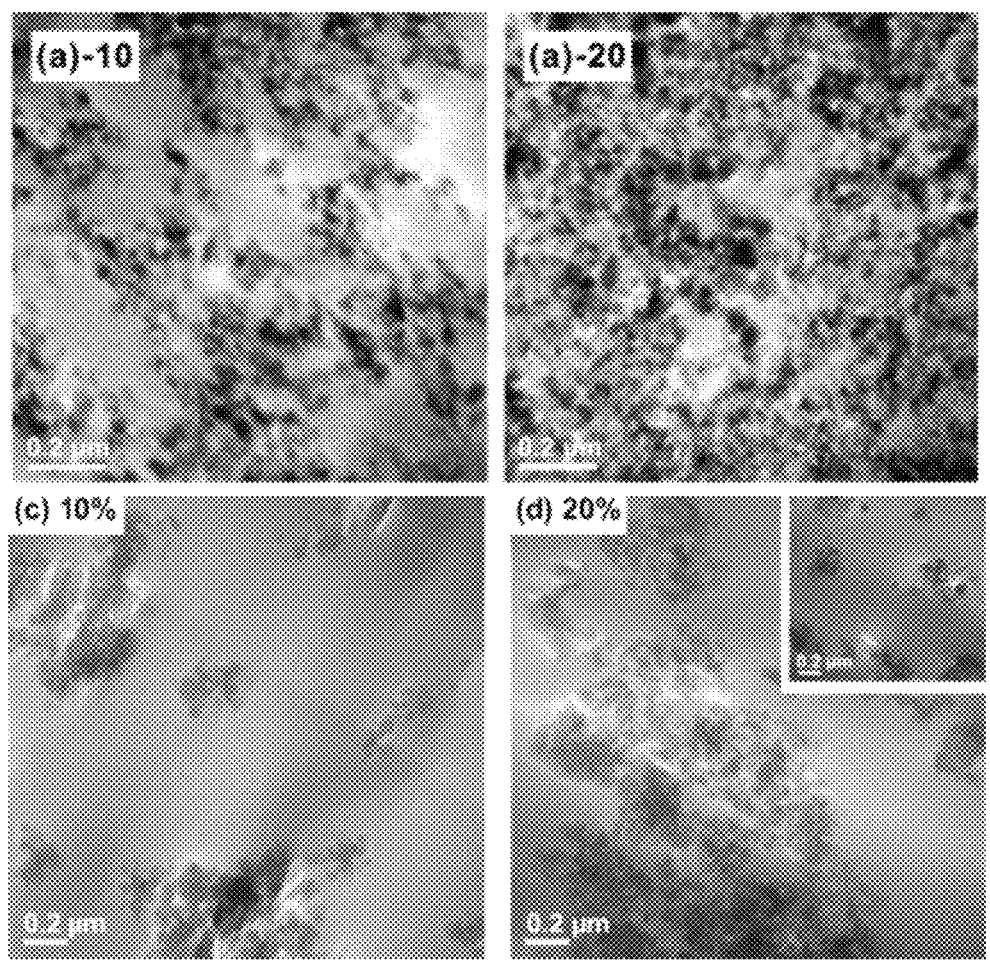
FIG. 4 provides examples of various nanocomposite morphologies.

The morphology of polymer nanocomposites can vary based on synthesis and treatment methods, with drastic consequences on transport properties. Takahashi et al (*Polymer*, 47(21), 7519-7534) illustrated the various post-processing methods in a poly(ether imide)/fumed silica nanocomposite on transport properties (see FIG. 4). Although Maxwell's prediction was obeyed in some cases, addition of silica particles had inconsistent effects on the permeability. Transmission electron microscopy (TEM) showed different morphological states as the origin of these differences.

Further, the addition of a penetrant that would be present during a membrane separation introduces additional complexities. For example, it has been demonstrated that PMA films loaded with silica nanoparticles may have good dispersion upon spin casting, but phase separation may occur in the presence of solute.

In one aspect, the present disclosure provides methods. These methods include contacting a fluid having at least two components to a membrane under such conditions such that one of the at least two components of the fluid is preferentially passed through the membrane, the membrane comprising a plurality of graft nanoparticles.

Further details of graft nanoparticles are described elsewhere herein; a graft nanoparticle suitably comprises a nanoparticle (a) having an average cross-sectional dimension (exemplary cross-sectional dimensions include diameter, thickness, radius, and height) in the range of from about 1 nm to about 50 nm and (b) having a population of polymer chains attached thereto, and the plurality of graft nanoparticles being arranged in a lattice structure.

The lattice structure may be periodic (in one, two, or three dimensions) in nature. The structure may also be achieved by self-assembly of the graft nanoparticles or by directed assembly of the graft nanoparticles. Structure may also be achieved by modulating environmental conditions (e.g., temperature, solvent, humidity, and the like) so as to encourage graft nanoparticle assembly.

The nanoparticle portion of a graft nanoparticle may have an average cross-sectional dimension (e.g., diameter, radius) in the range of from about 2 nm to about 50 nm, or even in the range of from about 3 nm to about 8 nm. Nanoparticles having a cross-sectional dimension of about 10 nm to about 15 nm or about 20 nm are also suitable. Solid and core-shell nanoparticles are all considered suitable.

Suitable nanoparticle materials include, e.g., $SiO_2$, $TiO_2$, and the like. $SiO_2$ is considered especially suitable, but is not the exclusive material for nanoparticles. Nanoparticle materials that are inert are considered suitable for some embodiments.

Other materials suitable for use as nanoparticles include metals, e.g., silver (Ag). Silver is considered particularly suitable because of its antimicrobial properties, which properties make silver very useful in filtration and purification applications. Barium titanate ($BaTiO_3$) is also suitable, as it is ferroelectric and also a strong material. Gold (Au) is also considered a suitable nanoparticle material.

Polymeric nanoparticles—including polymer beads (functionalized and otherwise)—are also considered suitable. Functionalized polymer nanoparticles are especially useful as they may be altered to control the softness of the nanoparticle by altering cross-linking. C-60 "Buckyballs" and other fullerenes are considered suitable nanoparticle materials. Particles that comprise alumina ($AlO_3$) and bromate ($BrO_3$) are also considered suitable, as those materials are characterized as having comparatively high degrees of thermal conductivity.

For some industrial applications, $TiO_2$ particles are especially suitable, owing to the particles' ability to withstand high pressure environments such as those found in typical gas/vapor processes. These materials are also resistant to cleaning materials that are used on the membrane (e.g., a caustic base solution, such as NaOH) to remove any fouling that occurs. This is fairly universal across all processes, so the graft-nanoparticle assembly layer would not be affected by cleaning processes. As described elsewhere herein, silver nanoparticles are useful in water separations membranes due to their natural antimicrobial properties.

A user may modify at least a portion of the surface of a nanoparticle so as to facilitate grafting or attachment of polymer chains to the surface; such modifications are well known to those of ordinary skill in the art. Similarly, one may also, supply, synthesize, or modify a polymer chain or a linker to facilitate attachment between the polymer chain and the nanoparticle.

In some embodiments, a polymer chain is one that is characterized as being hydrophobic, e.g., polystyrene, poly(methyl methacrylate), and the like. In other embodiments, a polymer chain may be one that is characterized as being hydrophilic, e.g., poly(vinyl alcohol), poly(ethylene oxide), and the like. PMA and PMMA are both considered particularly suitable—but non-limiting—examples of polymer chains.

The average length of the population of polymer chains attached to the nanoparticle may, in some embodiments, be between about 20% and about 200%, between about 30% and about 190%, between about 40% and about 180%, between about 50% and about 170%, between about 60% and about 160%, between about 70% and about 150%, or even between about 80% and about 140% of the cross-sectional dimension of the particle. A polymer chain average length of between about 85% and about 115% of the cross-sectional dimension of the nanoparticle is considered suitable; in some embodiments, the average length of the population of polymer chains attached to the nanoparticle is between about 95% and 105% of the cross-sectional dimension of the nanoparticle, and in other embodiments, the polymer chains have an average length that is equal to or about equal to the cross-sectional dimension of the nanoparticle. In still other embodiments, the average length of the population of polymer chains attached to the nanoparticle may be from 10% to 1000% of the cross-sectional dimension of the nanoparticle.

The molecular weight of a graft chain may be, e.g., from 10,000 to 1,000,000 g/mol. The weight may be the chain entanglement length for a given polymer species. Some suitable, illustrative polymers/end groups include (without limitation): Poly(n-alkyl methacrylates), e.g., poly(methyl methacrylate), poly(n-butyl methacrylate), pentyne derivatives and other polyacetylenes, e.g., poly(4-methyl-2-pentyne) [1], polyimides, cellulose acetate/polysulfone (particularly suitable for water treatment applications). Alkane, alkene, and alkyne-containing chains are all considered suitable.

A user may select a polymer based in part on the application under investigation. For example, polyacetylenes have been shown to have increased free volume and have useful natural gas separations properties, while linear fluorinated polymers (e.g., Teflon™) have high chemical resistance. Polyimides may be used for gas separations; any of the foregoing is a suitable polymer graft for a gas separations process.

End groups suitable for graft chains include, e.g., amine groups, high surface-tension groups, carboxyl groups, lower-surface-tension groups, e.g., fluorine groups. An end group may serve two purposes: (1) changing the surface tension of the chain end, giving control of the uptake free energy (i.e., manipulating permeability) and (2) increasing the solubility of a particular component relative to a normal polymer. As one example, fluorine groups have a very low surface tension, so there is a higher cost to make a polymer-air interface. Amine groups have a high solubility for carbon dioxide, so a membrane used for carbon capture might use these groups. Other end groups could also be added, again depending on the process.

A polymer chain may be attached to the surface of a nanoparticle via covalent bond, ionic bond, hydrogen bond, orbital interactions, coordination bonds, electrostatics, or by other bonds or techniques known to those of ordinary skill in the art.

The following are illustrative, non-limiting graft chemistries:

Atom-Transfer Radical-Polymerization (ATRP); both graft-from and graft-to (attaching fully-grown chains to particle after synthesis). This technique may be used with any transmission metal with vacant D-orbital as catalyst; Cu(I) is one useful catalyst for this process.

Reversible Addition Fragmentation Chain-Transfer (RAFT) polymerization; graft-from method (grow chains from the nanoparticle). This technique does not require a metal catalyst, and the initiator is easy to remove. This method also allows for control of molecular weight/polydispersity, and may be used to create design complex structures, block co-polymers, and the like. (This technique may sometimes be considered a type of ATRP.) The technique may be performed in many different solvents, at varied temperature ranges and reduces risk of reactions with side groups.

The choice of graft chemistry will depend on the user's needs. In many applications, both techniques are considered suitable, depending on the specific polymer and required product specs.

A graft nanoparticle according to the present disclosure may have a polymer chain density of, e.g., from about 0.01 to about 1 polymer chains per $nm^2$ of nanoparticle surface, or from about 0.05 to about 0.3 polymer chains per $nm^2$ of nanoparticle surface. A graft nanoparticle may also be characterized as being from about 0.01 vol % to about 50 vol % particle, meaning that for a grafted nanoparticle, the volume of the core particle to which the chains are grafted represents from about 0.01 to about 50% of the total volume occupied by the grafted nanoparticle. Again, all ranges disclosed herein are illustrative only and do not limit the scope of the present disclosure or any claims appended thereto.

As described elsewhere herein, the disclosure provides contacting the membrane to a fluid. A variety of fluids (liquids and gases) may be processed by the disclosed membranes. Fluids that include natural gas (e.g., as a component of the fluid) are considered especially suitable, as the disclosed technology may be used to separate natural gas from a fluid. Fluids may also include a species (e.g., a biomolecule), which species may be preferentially passed through the membrane, or, alternatively, may be preferentially retarded by the membrane. As one such example, a membrane for use in food storage applications may be configured to retard oxygen passage.

A membrane may be configured so as to preferentially pass therethrough a pre-selected component of the fluid. As one example, a membrane may be configured so as to preferentially pass natural gas therethrough while restricting passage of water. A membrane may also be configured to pass a single selected component of natural gas therethrough.

Polymer chains used in the disclosed technology may include moieties or other modifications (e.g., a charge, an aromatic group, a metal, nitrogen, boron, sulfur, and the like). As one example, polymer chains may include a biomolecule, such as a protein, an enzyme, a nucleic acid, and the like. As another example, some of the population of polymer chains may include a polar group, an ionic group, an aromatic group, and the like.

Membranes according to the present disclosure may also include a solvent, e.g., THF. Polar, aqueous, and non-polar solvents are all suitable. As described elsewhere herein, solvent may—without being bound to any particular theory—effect formation of spaces or channels between graft nanoparticles.

Structures (e.g., membranes) may also include an additional amount of polymer (sometimes termed "matrix polymer"). The additional polymer need not necessarily be attached or otherwise coordinated with the nanoparticles.

The matrix polymer may be the same as the polymer that is attached to the nanoparticles of the membrane. Alternatively, the matrix polymer may differ from the polymer that is attached to the nanoparticles of the membrane in terms of composition, size, or both. Again—and without being bound to any particular theory—the matrix polymer may be a comparatively stiff or resilient polymer so as to confer a particular mechanical property on the membrane. The matrix polymer may be hydrophilic, hydrophobic, or even amphoteric, depending on the user's needs.

Matrix polymers are suitably polymers that do not cause any sort of phase separation of the grafted particles. A user may use as the matrix polymer the same polymer used as the nanoparticle graft (e.g., PMA), but this is not a requirement. For adding strength or stiffness, a glassy polymer (e.g., polystyrene or a polyacetylene) may be used.

A user may collect a component of the fluid that is preferentially passed through the membrane; a user may also collect fluid that is not preferentially passed through the membrane. Collection may be performed by draining into a vessel, pipe, or other destination. Collection may also be accomplished by condensing, trapping, evaporating, chelating, collecting via reduced pressure or vacuum, or by otherwise capturing.

The present disclosure also provides systems, which systems may be applied to separation or purification applications. A system according to this disclosure may include a chamber having an inlet, the inlet in fluid communication with a first membrane, the first membrane comprising a plurality of graft nanoparticles, a graft nanoparticle comprising a nanoparticle (a) having an average cross-sectional dimension in the range of from about 1 nm to about 50 nm and (b) having a population of polymer chains attached thereto, and the plurality of graft nanoparticles being arranged in a lattice structure.

Features of suitable membrane structures and suitable graft nanoparticles are described elsewhere herein. For the sake of brevity, these features are not again repeated here.

A system may include a source of fluid in fluid communication with the inlet. The fluid may be, in some instances, a fluid from which a user may seek to isolate one or more components. As one example, the fluid may be a fluid from which the user may wish to separate or isolate one or more components. In other embodiments, the fluid may be a fluid used to flush, clear, or otherwise clean the membrane.

As described elsewhere herein, a fluid may include at least two components, one of the at least two components of the fluid being preferentially passed through the first membrane as compared to another of the at least two components. Also as described elsewhere herein, the first membrane may be configured so as to preferentially pass natural gas therethrough. It should be understood, however, that natural gas is not the sole component that a membrane may preferentially pass (or preferentially retard), as a membrane may be configured to preferentially pass (or retard) virtually any component of interest. Groundwater, oil (crude or refined), distillates, biological fluids, and the like are all considered suitable fluids.

A system may include a volume configured to collect material preferentially passed through the first membrane. Such a volume may be, e.g., a vessel, a basin, a pipe, a balloon, a funnel, a cup, and the like. A system may also include a volume configured to collect material that is not preferentially passed through the first membrane. Collection may be performed on a batch basis or on a continuous basis.

Systems according to the present disclosure may include a second membrane. The second membrane may be the same as or similar to the first membrane. Alternatively, the second membrane may differ from the first membrane in terms of composition, dimension, or both. A membrane may have a cross-sectional dimension in the range of, e.g., from about 20 nm to about 2000 nm, about 5000 nm, about 10,000 nm, or even greater. Membranes may be formed as discs, squares, ovals, or any other shape suitable to the user's needs.

In some embodiments, under the same conditions, the rate at which the first membrane passes a component is within about 10% of the rate at which the second membrane passes that same component. In some embodiments, under the same conditions, the rate at which the first membrane passes a component is within about 5% of the rate at which the second membrane passes that same component. In other embodiments, the rate at which the first membrane passes a component is within about 1% of the rate at which the second membrane passes that same component. Alternatively, the rate at which the first membrane passes a component is 1.1, 2, 3, 4, 5, 10, 20, 50, 100, 200, 500, 1000, 10,000, or even 100,000 times the rate at which the second membrane passes that same component. The first membrane may also pass a component more slowly than does the second membrane, e.g., $1/1.1$, $1/2$, $1/3$, $1/4$, $1/5$, $1/10$, $1/20$, $1/50$, $1/100$, $1/200$, $1/500$, $1/1000$, $1/10000$, or $1/100000$ times the rate at which the second membrane passes the component.

A user may arrange membranes in series so as to effect separations of different components from a particular sample. For example, a user may sequence membranes so as to use a first membrane that preferentially passes Component A present in a sample. The user may then draw off the Component A-rich permeate from behind the first membrane. The second membrane may preferentially pass Component B present in the sample, and the user may then draw off the Component B-rich permeate from behind the second membrane. In this way, the user may arrange membranes in a staged-type system.

A user may also sequence multiple membranes of the same type so as to isolate and purify a single component from a sample. As one example, a user may sequence membranes so as to use a first membrane that preferentially passes Component A present in a sample. The user may then contact the Component A-rich permeate from that first membrane to a second membrane that identical to the first membrane, thus giving rise to a permeate that is further enriched in Component A. A user may use a series of membranes that differ in their permeability and selectivity for Component A so as to quickly produce moderately-enriched streams of Component A and then further refine those streams as needed. In this way, the disclosed technology allows for sequenced separation systems and methods.

The present disclosure also provides additional methods. These methods suitably include assembling a plurality of graft nanoparticles into a structure, a graft nanoparticle comprising a nanoparticle (a) having an average cross-sectional dimension in the range of from about 1 nm to about 50 nm and (b) having a population of polymer chains attached thereto, the plurality of graft nanoparticles being arranged in a lattice structure.

The methods may also include selecting one or more of the nanoparticles, the polymer chains, a solvent, or a moiety attached to the polymer chains so as to construct a structure (e.g., a membrane) that preferentially passes therethrough a pre-selected component of a fluid (e.g., natural gas, a sulfur-containing compound) comprising the pre-selected component and at least one additional component. In this way, a user may select a configuration of nanoparticles, polymers, solvent, and polymer moieties that is tailored to preferentially pass (or retard) passage of one or more pre-selected components.

A structure may have the form of a membrane. A structure may also have the form of a monolith, puck, cartridge, sheet, film, and the like. It should be understood that the present disclosure and the appended claims are not limited to membrane forms and that other forms besides membranes are within the scope of this disclosure; description of embodiments using membranes are intended to be illustrative and do not limit the scope of this disclosure. A structure according to the present disclosure may have an aspect ratio of 1:1, 1:5, 1:100, 1:1,000, 1:10,000, 1:100,000, 1:1,000,000, 1:10,000,000, or even 1:1,000,000.

A membrane may be constructed such that the membrane passes the pre-selected compound (in a sample) at a rate of from 1.001 to about 10,000 times the rate at which the membrane passes the remainder of the sample, or from 2 to about 9,000 times the rate at which the membrane passes the remainder of the sample, or from 10 to about 1000 times the rate at which the membrane passes the remainder of the sample, or from 20 to about 500 times the rate at which the membrane passes the remainder of the sample, or from 100 to about 200 times the rate at which the membrane passes the remainder of the sample.

The present disclosure also provides sensors. Without being bound to any particular theory, it has been observed that assemblies of graft nanoparticles as described herein may experience a physical change upon exposure to an agent. For example, an assembly of a first type of graft nanoparticles may change color (or opacity, polarization, or some other optical characteristic) upon contact with methane gas. The change may be proportional to the concentration of the methane gas. An assembly of a second type of graft nanoparticles may exhibit a physical change (which may be the same or different from that of the first type of graft nanoparticles) when contacted with ammonia gas. By correlating changes in the physical state of the graft nanoparticle assembly to the presence of an agent, a user may thus use the assembly of graft nanoparticles to detect the presence of that agent.

Without being bound to any particular theory, block copolymer materials may order (or disorder, in some cases) on solvent annealing, i.e., the addition of a solvent material to a graft nanoparticle assembly causes the formation of a structure that differs in order from the order of the assembly before solvent introduction. The same is also true of the disclosed materials; again without being bound to any particular theory, if a chain has to stretch severely and still cannot balance the surface tension price, then the system would rather disorder than pay two separate penalties. If a solvent is added, the surface tension price goes down, and an ordered state may then be more energetically favorable. This behavior may be independent of solvent and may depend on the polymer chemistry being used (molecular weight, graft density, end groups, and the like).

A user may determine the sensitivity of a given assembly of graft nanoparticles to an agent by constructing a library of assemblies of different graft nanoparticles, exposing those assemblies to the agent of interest, and assessing the physical changes experienced by the assemblies after contact with the agent. In this way, a user may construct a customized sensor device that is sensitized to detect one, two, or more agents of interest. For example, a device may comprise a panel or array of films different assembled graft nanoparticles, each of which films is selected for its sensitivity to a particular agent. In this way, a user may use the device to simultaneous assess a sample (e.g., ambient air, exhaled air, a blood sample) for the presence of multiple agents of interest.

A sensor according to the present disclosure may thus suitably include one or more assemblies (e.g., a membrane or lattice structure) of graft nanoparticles (as described elsewhere herein) and a detector sensitive to changes in the assembly of graft nanoparticles. For example, the sensor may comprise an optical device (e.g., a camera, a photon counter, a PMT, and the like) that detects an optical change in the assembly of the graft nanoparticles. The sensor may also include a source of illumination that illuminates one or more assemblies for ease of observation. The sensor may also be configured to detect a change in an electrical characteristic of an assembly as a result of the assembly's contact with an agent of interest, e.g., a change in resistance, current, capacitance, and the like.

A sensor device may comprise a chamber in which one or more graft nanoparticle assemblies are disposed, e.g., in separate wells, chambers, pods, or other volumes. The chamber may include an inlet, an outlet, or both, to allow for introduction and removal of a sample of interest. The device may also include a fan, impeller, or other implement to facilitate introduction and/or removal of sample from the graft nanoparticle assemblies.

Without being bound to any particular theory, one may postulate that the self-assembly of the particles grafted with moderate length polymer chains into ordered arrays creates interstitial spaces. The addition of the nanocomposite lattice has also been shown to increase both the diffusivity and solubility of low molecular weight penetrants when compared to existing pure polymer membranes. This, in turn, increases the available "free volume" within the film and creates channels, similar in spirit to transport channels in cell membranes, which facilitate penetrant diffusion.

The tunability of these transport channels represents a paradigm shift for this class of membrane materials. Without being bound to any particular theory or embodiment, graft nanoparticles that self-assemble—under at least some conditions—into a lattice structure are considered especially suitable.

Again without being bound to any particular theory, one may further theorize that a potential explanation for the increase in diffusivity is that the grafted particles self-assemble when cast in a film. Then, unlike a traditional composite where the density is altered due to polymers packing within the interstitial space between the filler particles, the grafted chains are unable to stretch and fill in these void spaces. As such, in the grafted system, depending on chain length and grafting density there may exist channels that facilitate transport of small penetrant molecules, analogous to a protein channel in a cell membrane.

As grafting density and/or chain length increases, the ability of the chains to stretch and pack between the particles would be increased until the system behaves as a conventional polymer. On the other hand, as grafting density and/or chain length decreases, the channels may increase in size until the system approaches analogous diffusion through silica powder. By adjusting the chain length, chain composition, and grafting density, one may tune the size and characteristics of these channels could theoretically be tuned. Thus, the present disclosure allows for newly-attainable control over diffusivity and permeability of nanocomposite membranes.

Illustrative Embodiments and Results

To illustrate the effectiveness of the disclosed technology, diffusivity (D) and partition coefficient (K) measurements for were performed for two model solutes (ethyl acetate, butyl acetate) in illustrative (non-limiting) polymethylacrylate-grafted silica NP (14 nm diameter spherical NPs) based membranes. The grafted chain molecular weight (50-150 kg/mol) and grafting density (0.1-0.66 chains/$nm^2$) were varied systematically in a series of samples.

Surprisingly, it was found that both D and K were larger in the self-assembled polymer-grafted NP structures than in the bulk polymer and in a physical (ungrafted) mixture of bare NP and polymer. These results were surprising, as conventional (Maxwell) composite theory predicts that both of these quantities should decrease upon addition of a non-interacting filler to a polymer. Further, the trends for the selectivity versus permeability—critical for membrane performance—show increases relative to both quantities found for the corresponding pure polymer.

Without being bound to any particular theory, one may postulate that the self-assembly of the polymer-grafted NPs into arrays with mesoscale order creates interstitial spaces which can only be filled by stretching and/or rarefaction of the grafted chains. Placing solute molecules in the center of these interstices relieves some of this stretching and hence is free energetically preferred. Again, without being bound to any particular theory, this may give rise to transport channels that facilitate penetrant solubility and diffusion in the membrane construct resulting in the observed increases in the solute's K and D relative to even the pure polymer.

The following is non-limiting disclosure related to an illustrative synthesis and characterization of the disclosed technology. (All materials were used as received.)

Neat PMA (MW=146,000 g/mole, MW/MN=1.18, Tg=14.6° C.) was purchased from Polymer Source. PMA-grafted silica particles (d=15±4 nm) with chain density of 0.097 chains/$nm^2$ and chain length 76,000 g/mole were provided by the Benicewicz group from the University of South Carolina.

Solvents isopropylacetone (MIBK), 99.5+%, and ethyl acetate (EtAC), 99.5+% were purchased from Acros Organics (Geel, Belgium). Zero-grade nitrogen gas was purchased from Tech Air (White Plains, N.Y.). Neat polymer solutions were 5.4 wt % PMA in MIBK. A small amount of Irganox 1010 (0.1 wt % of the final sample) was used to inhibit oxidative degradation. Grafted particles were dissolved in a 5.7 wt % solution of tetrahydrofuran (THF).

Transport property measurements were made using a modified quartz crystal microbalance (QCM) apparatus. QCM transducers are driven by a feedback control oscillator at the fundamental resonant frequency, fq, of a 1 inch diameter, AT-cut, 5 MHz quartz crystal with gold electrodes (Inficon, Inc.). Changes in mass (per unit area) on the crystal's surface, $\Delta m$, results in a change in resonant frequency, $\Delta f$. Changes to the transducer's resistance, $\Delta R$, are caused by external damping or energy dissipation within the added layer. Under the assumption that the added mass is rigid ($\Delta R=0$) and small, $\Delta m$ is linearly related to $\Delta f$ using the Sauerbrey equation.

Thin polymer films are cast on a quartz crystal placed in a flow cell and a carrier gas with variable penetrant concentration is passed over the films. The quantities $\Delta f$ and $\Delta R$ are recorded continuously via data acquisition software and two cells can be used simultaneously in a single experiment. Upgrades to the gas handling system included replacing the rotometers with gas mass flow controllers (Aalborg, Orangeburg N.Y.) to control the partial pressure of solvent vapor in the carrier gas. Saturated penetrant stream was created by bubbling dried nitrogen gas through pure liquid ethyl acetate (EtAC) through two successive glass frits. The saturated stream was then quantitatively mixed down by adding a known mass flow of pure nitrogen. The flow controllers were operated with a programmable DC power supply so that experiments can be controlled manually or through a computer interface.

An alternative crystal cleaning protocol was: (1) remove dust with nitrogen blower; (2) place crystals in a Pyrex™ dish, add 12 ml sulfuric acid, then 4 ml hydrogen peroxide (makes a 3:1 piranha solution); (3) remove crystals after 1 minute; (4) rinse with DI water; (5) rinse with methanol; (6) repeat steps 4 & 5; (7) dry with nitrogen blower; (8) clean with UV-Ozone oven for 15 minutes; (9) blow once more with nitrogen.

To spin films, one may perform the following protocol: (1) prepare polymer solution (neat polymer or grafted particles dissolved in tetrahydrofuran, THF) (concentrations may be, e.g., less than about 5 wt % polymer/particles); (2) filter solution (e.g., with 0.2 um PTFE filter); (3) align clean crystal on Laurell spin-coater chuck; (4) flood crystal surface with polymer/particle solution; (5) spin for 30 s-1 min between 1000-15,000 rpm, adjusting acceleration for solution viscosity and desired film thickness.

As received quartz crystals were cleaned with a piranha solution (3:1 ratio of concentrated sulfuric acid to 30% hydrogen peroxide) for approximately 45 seconds. The crystals were then rinsed liberally with deionized water and then cleaned in a UV/$O_3$ oven for 10 minutes. Bare crystal resonant frequency, $f_q$, and resistance, $R_q$, were recorded before spin-coating the membrane films and to check for crystal integrity. Values of $f_q$ and $R_q$ between 5 MHz and 8$\Omega$, respectively indicate a good crystal, whereas $R_q$ values larger than 10 $\Omega$ indicated contamination or damage.

Next, films were cast on the cleaned quartz crystals by spin coating. For neat PMA films, a PMA/MIBK solution was spun at 1500 rpm for 1 minute, yielding a thickness of ~600 nm. Pure grafted particles (i.e., no additional matrix PMA was added to the particles) were spun from a particle/THF solution at 1500 rpm for 1 minute, yielding a thickness of ~400 nm. All films were then thermally annealed at 110° C. under vacuum for 36 hours and then reloaded into the flow cells.

Dry film frequency, $f_F$, and resistance values, $R_F$, were recorded and then the films were solvent annealed for 48 hours by flowing 50 sccm of saturated EtAC vapor (bubbler temperature was held at 0° C.) over the films. The films were re-dried by flowing pure nitrogen at 50 sccm over the films for 12 hours. Film thickness was measured via profilometry after all sorption experiments were completed. Frequency uncertainty due to loading and unloading the crystals was negligible and changes in resistance were less than 0.6$\Omega$, indicating films were rigid and loss free and thus justifying the use of the Sauerbrey equation. Penetrant weight fraction in the film was calculated. Partition coefficients were calculated as well.

Annealing may also be effected by, e.g., (1) placing sample in a QCM crystal holder, flowing 50 sccm nitrogen for 24 hours; (2) switching to 50 sccm solvent saturated (0° C.) vapor for 24 hours; (3) switching to 50 sccm nitrogen for 24 hours.

For QCM analysis, one may (1) program flow controller power supplies (e.g., 1 hour per step interval, voltage step increase for calculated desired concentration step change); (2) Record frequency, delta frequency and resistance; and (3) perform further data analysis. (Further information regarding procedures and analysis may be found in Janes, D. W., Kim, J. S. and Durning, C. J. 2012, *Industrial & Engineering Chemical Research*, pp. 8765-8773.)

Using QCM, values of $K(\omega 1)$ and D of ethyl acetate for pure poly(methyl acrylate) and PMA-grafted silica nanospheres were measured. Both systems exhibited Fickian diffusion and experimental design provided for operation within the linear response limit. Data for pure PMA matched previously work by Fujita. $K(\omega 1)$ and D values for the grafted particles were larger than neat PMA, which increased values were unexpected.

As described elsewhere herein, one possible, non-limiting explanation for the increase in these parameters is the existence of channels due to an inability of grafted chains to completely pack interstitial space between the self-assembled particles.

Further illustrative embodiments are described below—all materials were used as received. These illustrative experiments pertain to FIGS. 3-13.

Neat PMA (Mw=22,782 g/mole, DI=1.12, and Mw=134,535 g/mole, DI=1.16) and PMA-grafted silica (Mw=22,917, 58,926, 72,000, 103,182 & 158,215 g/mole, 0.1 chains/$nm_2$, and MW=50,000 0.32, 0.45 & 0.66 chains/$nm^2$,) where synthesized via RAFT by the Benicewicz Group from the University of South Carolina. The grafted films did not have any additional free polymer matrix. Tetrahydrofuran (THF) 99.5+% purity was purchased from Sigma Aldrich.

Penetrants ethyl acetate, 99.5+% purity and n-butyl acetate, 99.5+% purity were purchased from Acros Organics (Geel, Belgium). Zero-grade nitrogen gas was purchased from Tech Air (White Plains, N.Y.). All polymer solutions were between 25 and 50 mg/ml THF. The antioxidant Irganox 1010 was supplied by BASF (Ludwigshafen, Germany) and added to the solution to give a concentration of 0.1 wt % Irganox relative to sample mass to minimize polymer oxidation during subsequent thermal annealing.

Transport property measurements were made using a quartz crystal microbalance (QCM) setup. QCM transducers were driven at the fundamental resonant frequency by a feedback control oscillator. QCM crystals (1-inch diameter, AT-cut, 5 MHz nominal frequency) with gold electrodes were purchased from Inficon Inc.

As received crystals were immersed in piranha solution (3:1 ratio solution of concentrated sulfuric acid to 30% hydrogen peroxide solution) for approximately one minute. The crystals were then rinsed with deionized water and methanol and cleaned in a UV/$O_3$ oven for 15 minutes. Bare crystal resonant frequencies fq and resistances Rq were recorded prior to spin coating polymer films to check for crystal integrity and "taring" for use as a microbalance. Crystals with Rq greater than 10 $\Omega$ indicate damage or contamination, and were either recleaned or discarded. Polymer films were cast on the cleaned quartz crystals via spin coating.

Samples spun at 1200 rpm for 50 seconds yielded thicknesses of ~500 nm for neat PMA and ~350-400 nm for grafted particles Films were then annealed at 40° C. under vacuum for 2 hours to remove any remaining spinning solvent and returned to the QCM flow cells. Dry film frequencies $f_f$ and resistances Rf were recorded before annealing the films under a saturated penetrant vapor for 12 hours.

Films were then redried using nitrogen for 24 hours. Mass added (per unit area) onto a crystal's surface depresses the crystals resonant frequency, and external damping increases the crystal resistance. In the limit that the added polymer film is rigid and the mass uptake $\Delta m$ is small, the response is linear and related to material properties based on the Sauerbrey Equation. $\Delta f$ and $\Delta R$ are recorded continuously via data acquisition software to allow for in situ measurement of penetrant mass loading.

Crystals were held at 25° C. for all experiments. Film thicknesses were measured using a Datek contact profilometer and confirmed with a J. A. Wollam spectroscopic ellipsometer using a generalized Cauchy model fit. Atomic force microscopy (AFM) images were taken using a Brucker AFM and analyzed using Gwyddion software to qualitatively measure the nanocomposite ordering.

A saturated penetrant stream is created by bubbling dried and filtered nitrogen gas through pure liquid penetrant through successive fritted gas washers at a known temperature, effectively controlling the partial pressure of the stream. This saturated stream is mixed down with a known mass flow of pure nitrogen, allowing for improved experimental control of penetrant partial pressure.

Nitrogen mass flows were controlled using digital mass flow controllers (Aalborg, Orangeburg N.Y.). Differential sorption experiments were conducted by incrementally raising the flow rate of dried nitrogen to the bubblers, effectively increasing the partial pressure of penetrant in the vapor bulk.

Figure 5:
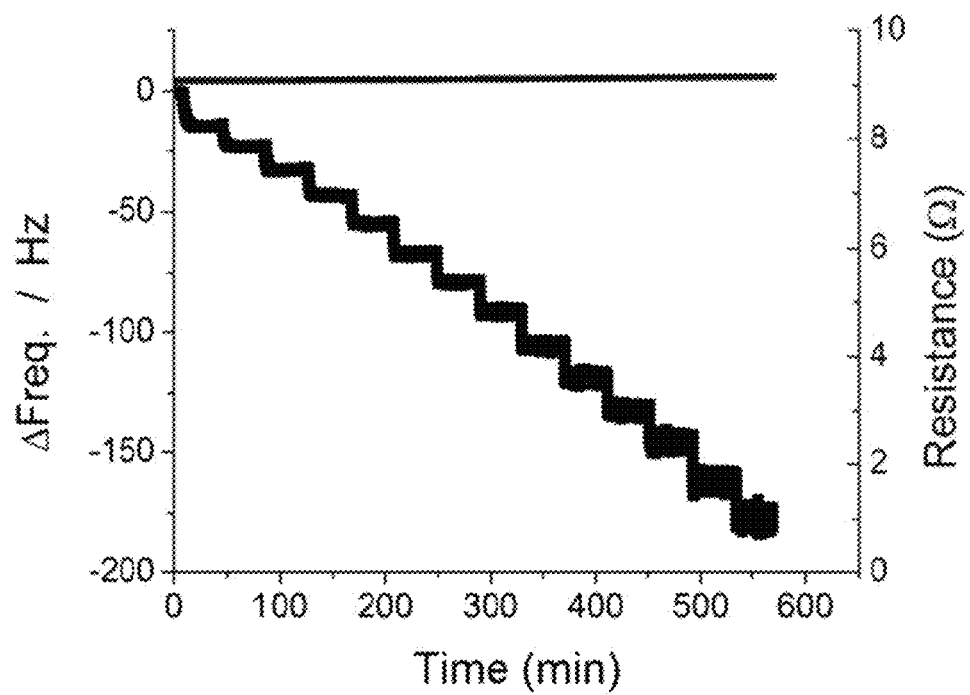
FIG. 5 provides illustrative frequency and resistance change data.
Figure 6:
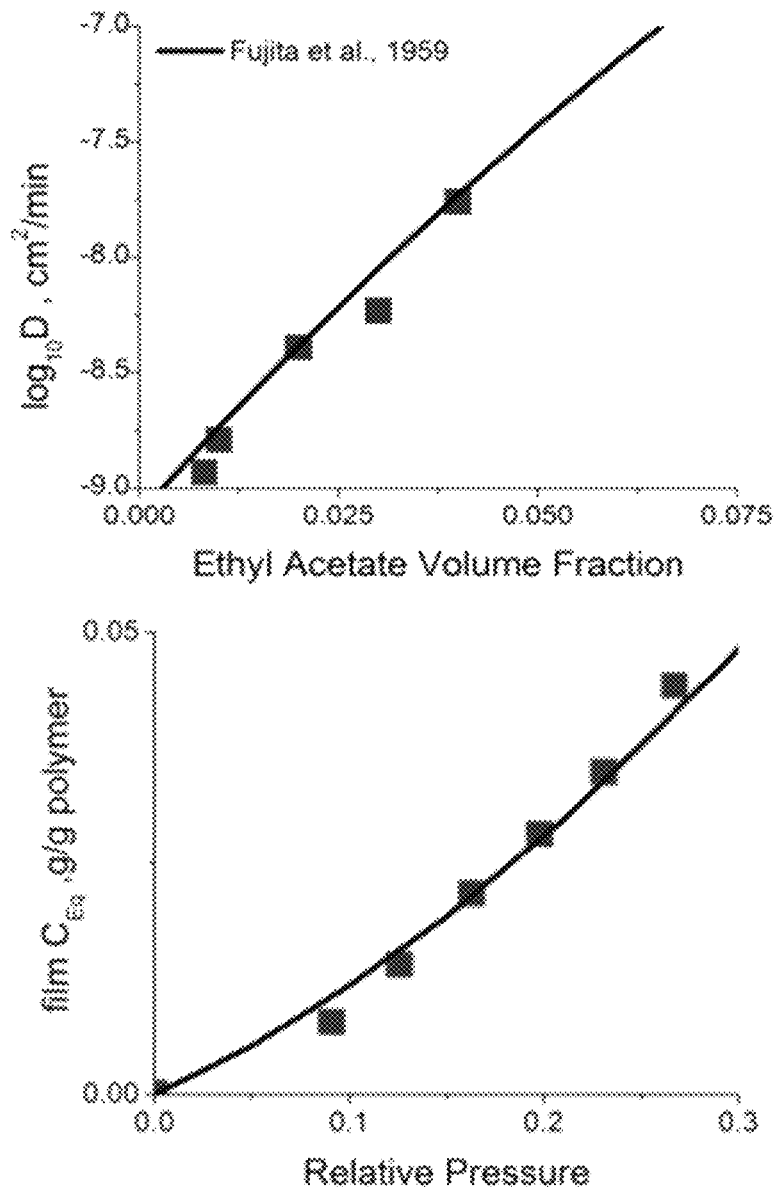
FIG. 6 provides a comparison of (a) diffusivity and (b) solubility measurements with accepted literature data.

FIG. 5 shows multiple interval sorption data, where the solvent vapor pressure is increased progressively in small steps. The data have been averaged using local signal averaging to reduce experimental noise. Note that crystal frequency fluctuations become larger with increasing solvent concentrations, limiting the accuracy of experiments for relative penetrant pressure ($P_{sol}/P_{sat}$) above 0.35: these fluctuations likely arise because the viscous dissipation terms increase. For each experiment, the frequency drops sharply upon initial penetrant uptake and eventually relaxes to an equilibrium, which required less than one hour for both neat and grafted PMA samples. Diffusivity and equilibrium solubility values for ethyl acetate in neat PMA are shown in FIG. 6. These are in good agreement with literature values.

Figure 7:
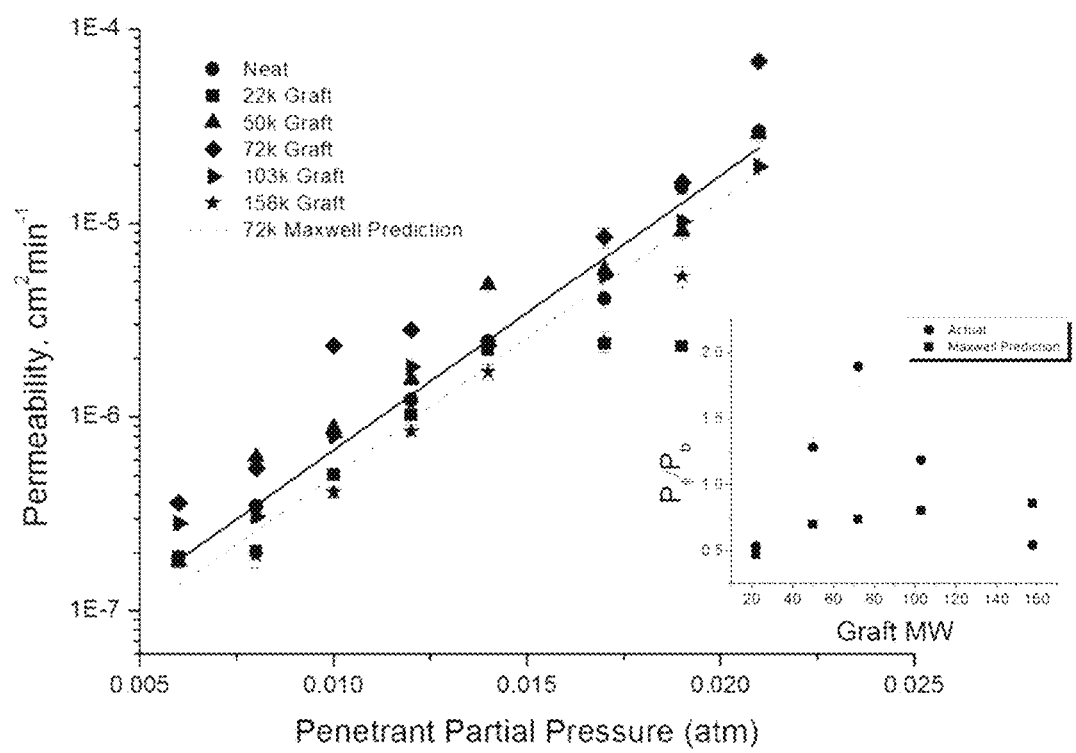
FIG. 7 provides a comparison of permeability with molecular weight. The dotted line represents Maxwell's prediction for a 72k graft; inset: a "Volcano Plot" comparing the permeability of various graft molecular weights (Pφ) with that of the neat polymer (Pb) at Pp=0.017 atm.

FIG. 7 shows average permeability values versus penetrant partial pressure for a variety of low-density PMA graft molecular weights with fixed grafting density of 0.1 chains/nm$^2$. These data are normalized based on polymer mass.

Figure 8:
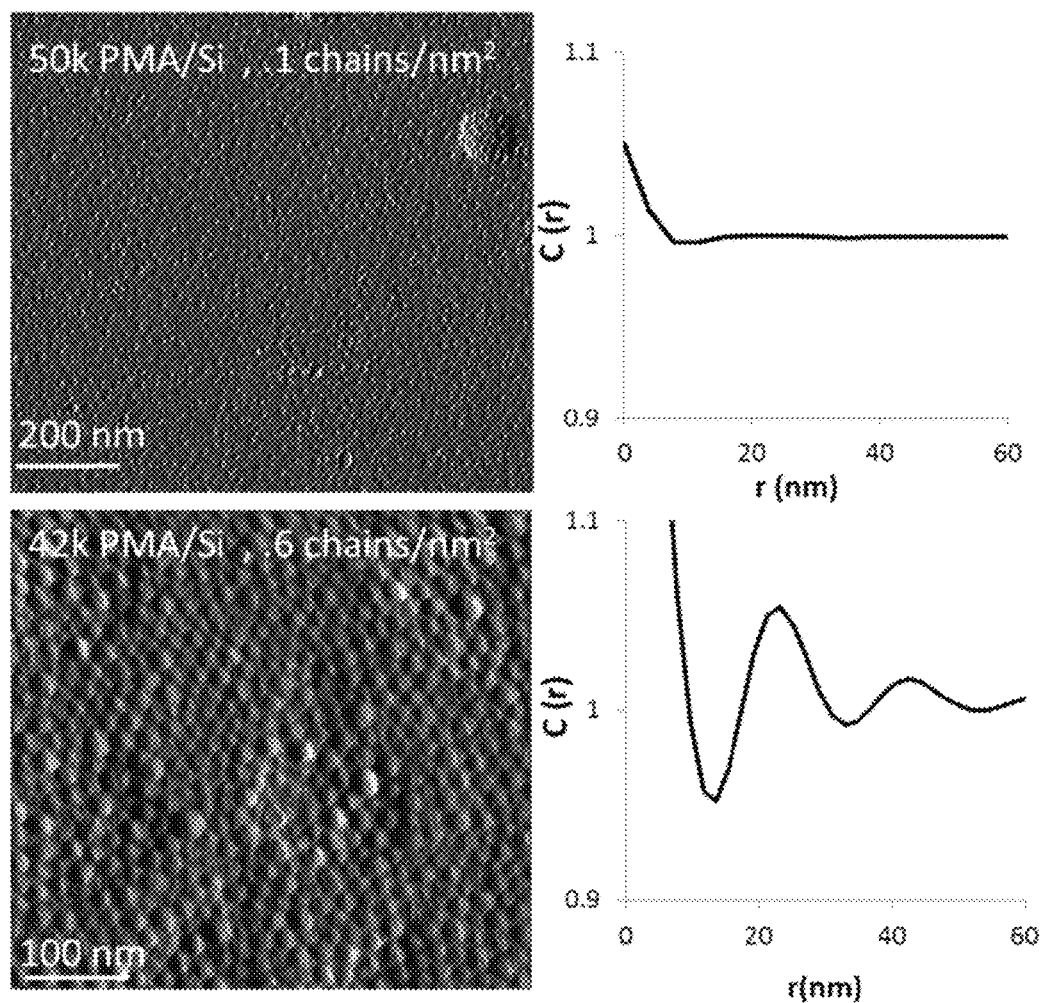
FIG. 8 provides peak force AFM images and corresponding autocorrelation functions of low and high graft density composites.

Permeability displays non-monotonic behavior with increasing molecular weight, with 50k and 72k grafts having elevated permeabilities relative to the neat polymer melt, contrary to conventional composite theory. This is a result of an increase in both K and D, indicating both increased solubility per unit polymer mass and faster uptake kinetics. 103k grafts show no detrimental change in permeability due to particle addition. A representative AFM image and autocorrelation function of low graft density composites is shown in FIG. 8. The low grafting density samples showed only local order. Higher PMA grafting density samples of comparable molecular weight display a more ordered structure. This ordering is seen in grafted composites with densities as low as 0.3 chains/nm$^2$, which is comparable to graft densities reported to induce self-assembly.

Figure 9:
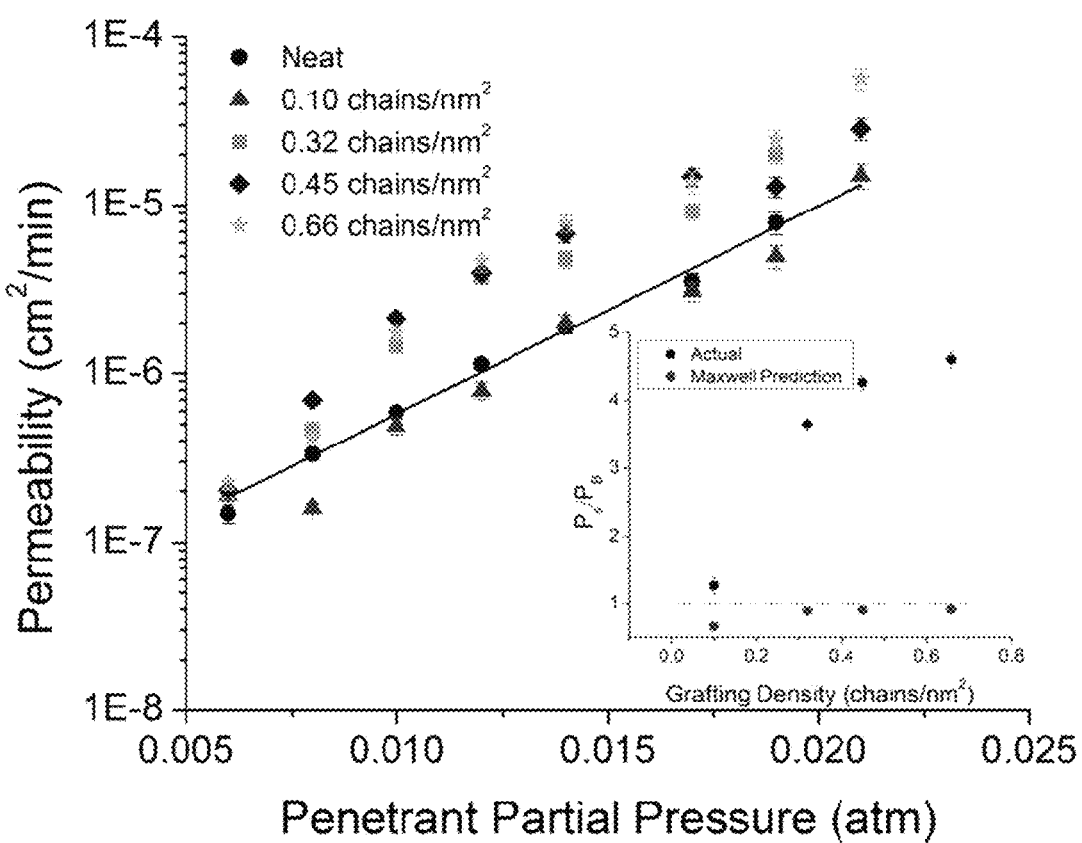
FIG. 9 provides a comparison of permeability with increasing polymer graft density. All polymer molecular weights are approximately 50k; inset provides a so-called "volcano plot" of permeability at Pp=0.014 atm.

Permeability measurements of composites with a 50k molecular weight brush and varying grafting densities are shown in FIG. 9. Increasing the grafting density to 0.32 chains/nm$^2$ increases the permeability to 350% of the neat melt (FIG. 9 inset); this continues to rise with increased graft density. Although both K and D increased for the lower grafting density samples, the substantial increase in the high grafting density samples is driven mostly by an increase in diffusivity.

Figure 10:
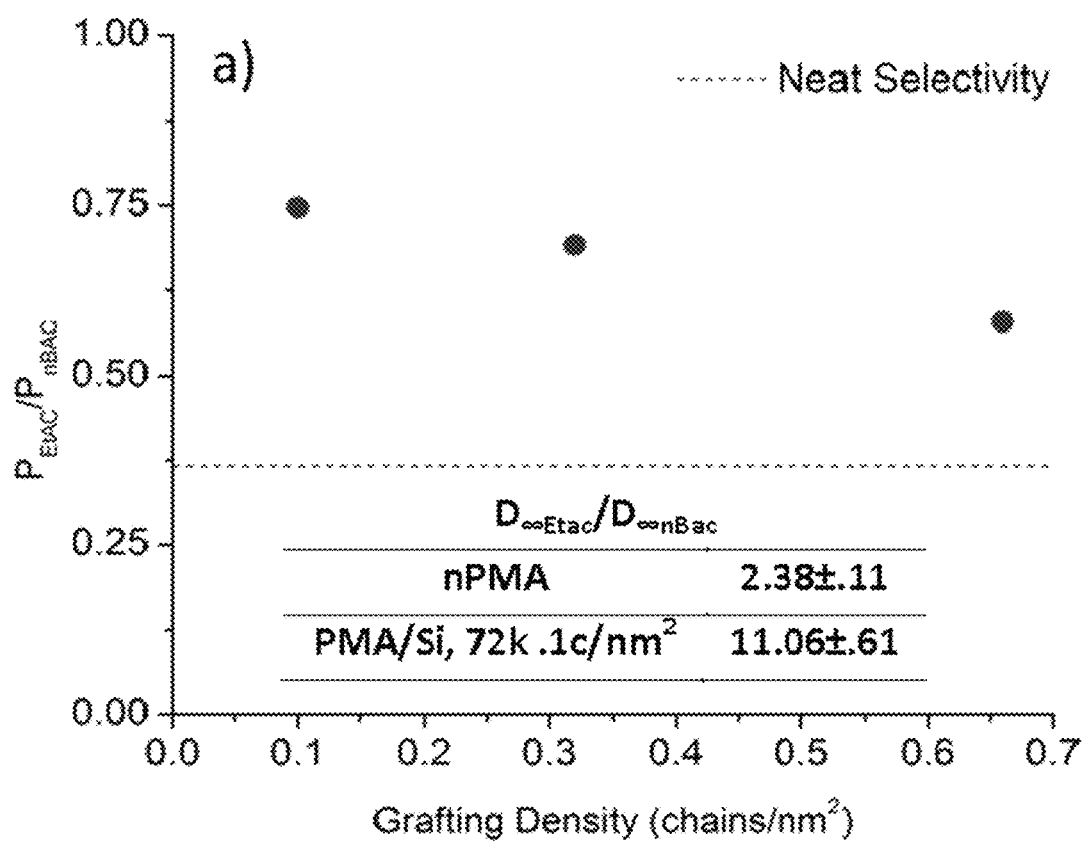
FIG. 10 provides ideal selectivity of PMA/Si composites as a function of grafting density—all brushes are approximately 50k; inset provides ratio of infinite dilution diffusion constants of ethyl acetate and n-butyl acetate.
Figure 11:
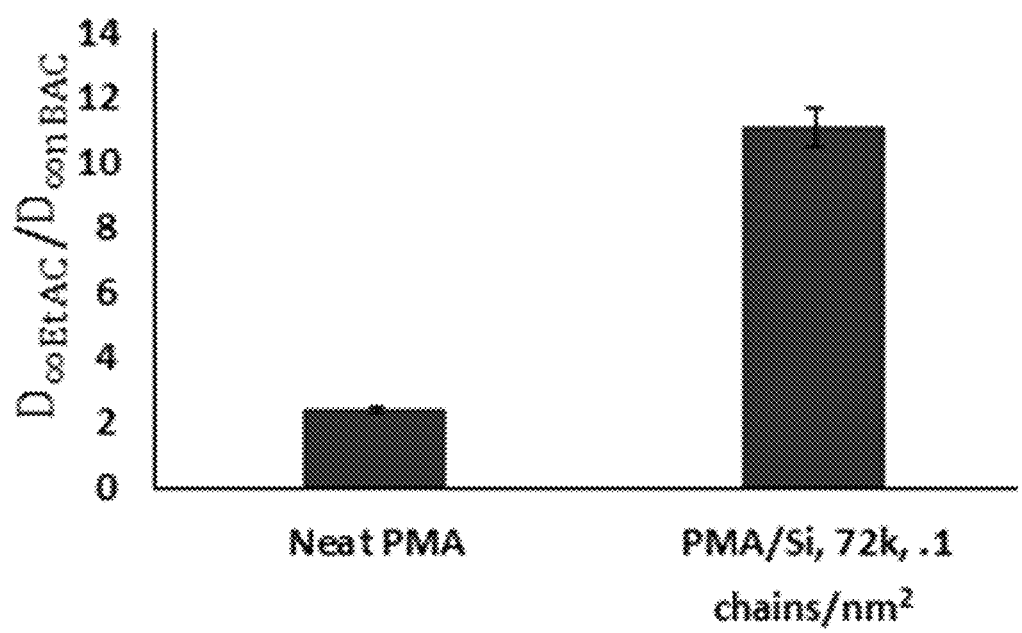
FIG. 11 provides further ideal selectivity data, related to FIG. 10.

Ideal selectivity measurements were performed by comparing the permeabilities of pure ethyl acetate and pure n-butyl acetate (i.e., penetrants were not in competition with each other). These results are shown in FIG. 10. The selectivity of ethyl acetate in neat PMA is <1, indicating the polymer favors uptake of the larger molecule (as evidenced by the ratio $D_{\infty EtAC}/D_{\infty nBAC}$ in the inset of FIG. 10 being greater than 1).

Without being bound to any particular theory, this suggests a process dominated by the solubility of the larger molecule, as diffusion normally favors smaller species. However, low graft density composites show a significant increase in ethyl acetate diffusion, with $D_{\infty Etac}/D_{\infty nBac}$ increasing by a factor of five. This is now indicative of a diffusion-limited process.

Figure 12:
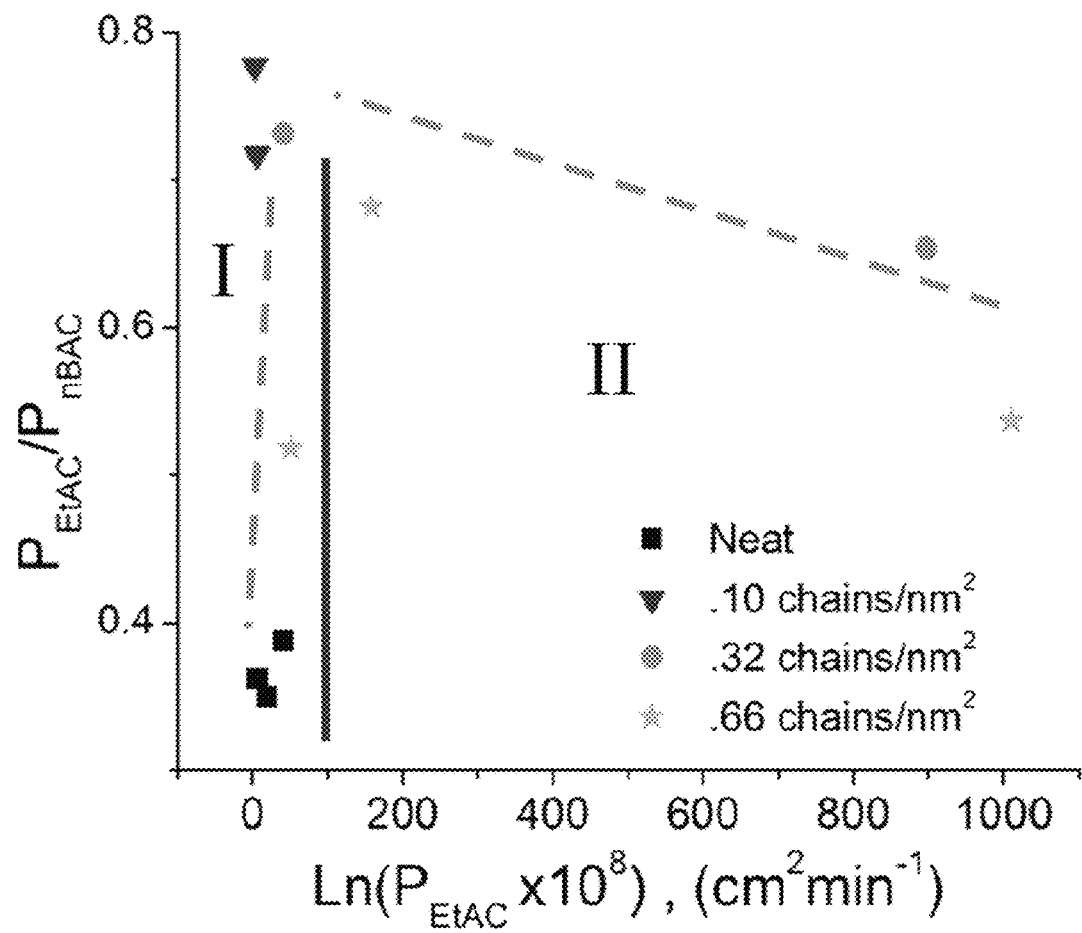
FIG. 12 provides a Robeson plot of neat PMA and selected PMA/Si composites with varying grafting densities.

The relationship between selectivity and permeability of composites with increased graft density is shown in FIG. 12. The first regime (I) represents an increase in both film permeability and selectivity relative to the neat polymer, while the second (II) shows a steady decline in selectivity as the permeability of the film is increased. This decrease is consistent with typical membrane performance and Robeson plots (see Robeson plot in FIG. 3).

The polymer grafts, however, have significantly increased both permeability and selectivity above the neat polymer. The first regime shows a sharp increase in selectivity without compromising permeability, which behavior has not previously been reported in literature.

Figure 13:
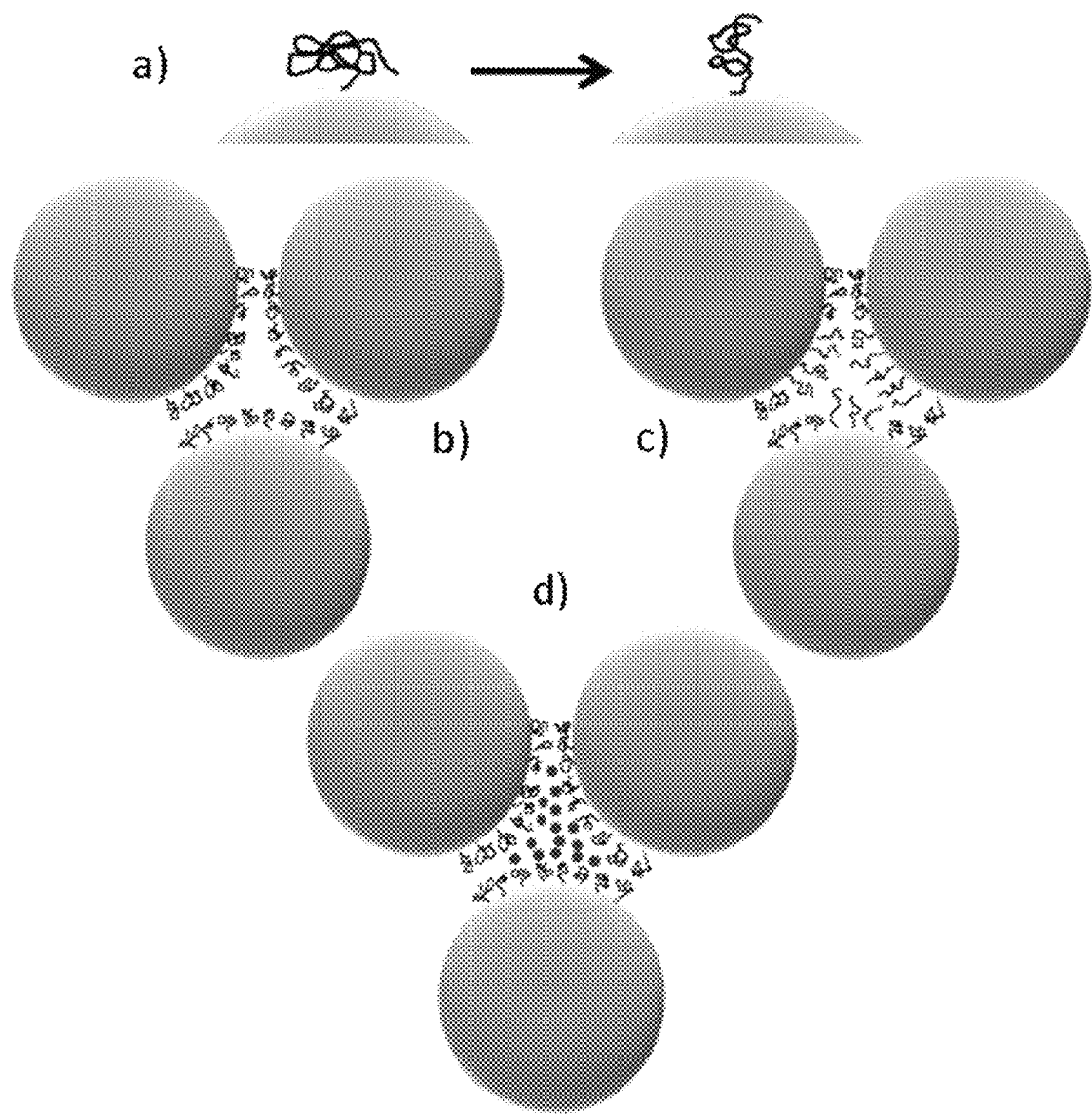
FIG. 13 provides polymer morphology (a) for a low graft density composite; note the polymer swells upon penetrant addition; (b) in high graft density composites, the brush suffers an interfacial tension and stretches into the interstitial void (c). This tension is relieved with penetrant uptake (d).

Without being bound to any particular theory, it is proposed that when the grafting density is high enough to induce self-assembly, a gap between the nanoparticles in the center of the void is created by triangular packing of the nanoparticles (FIG. 13). The grafted chains can either stretch to fill this gap, or pay the free energy penalty (surface tension) for creating a polymer-air interface.

Because surface tension should dominate, the nanoparticles approach each other by compressing the brushes at their points of closest contact. Additionally, the grafts stretch into the interstitial space to fill the gaps. Both these factors decrease the chain's configurational entropy and drives this self-assembled state to have a higher free energy than a polymer melt with no constraints. This can cause the chain to stretch from, e.g., 22.1 to 25 nm for a polymer with degree of polymerization N=1000 in theta solvent, which corresponds to chain stretching by a factor of approximately 1.15 for molecular weights with permeabilities of interest.

When solute is introduced, the solute goes into this void at the center and allows the chain to relax, which will in turn favor both solubility and diffusion. With increasing grafting density, one may suggest that the unfavorable free energy increases—this leads to an increase in permeability, but a reduction in selectivity, qualitatively explaining Regime II in FIG. 12.

For low graft densities the nanoparticles do not order and hence Maxwell-like behavior is expected. Intermediate between these two regimes, one may expect that maximum selectivity would occur just when the nanoparticles are on the verge of ordering. Here, the addition of a suitably-sized solute may cause the nanoparticles to order causing significant improvements to the selectivity.

Because of these unique properties, membranes according to the present disclosure may exhibit a selectivity between two penetrants—at a given permeability value—that is greater than the selectivity of the neat polymer for those penetrants by from about 1.01 times to about 50 times, or from about 1.10 times to about 10 times, or from about 1.2 times to about 3 times, or from about 1.3 times to about 2 times, or from about 1.8 times to about 2.1 times, or from about 1.8 to about 2.0 times, or even from about 1.4 to about 1.8 times.

One illustration of this is shown in FIG. 12, with particular reference to Regime I in that figure. As shown in the figure, the disclosed compositions exhibited—in one illustrative experiment—a selectivity between two exemplary penetrants (EtAC, nBAC) that was about 100% greater than the selectivity of the neat polymer at a given permeability value.

Membranes according to the present disclosure may also exhibit a selectivity that increases over a range of increasing permeability values. (This may be relative to the neat polymer.) For example, a membrane may exhibit a selectivity (between two penetrants) that increases by from 0.1% to about 500% over an increase in permeability of from about 0.01% to about 100%, or exhibit a selectivity that increases by from 1% to about 100% over an increase in permeability of from about 0.01% to about 500%, or even exhibit a selectivity that increases by from 5% to about 25% over an increase in permeability of from about 0.01% to about 100%. For example, a membrane may exhibit a selectivity (between two penetrants) that increases by from 90% to about 120% over an increase in permeability of from about 5% to about 20%, or exhibit a selectivity that increases by from 80% to about 100% over an increase in permeability of from about 220% to about 240%, or even exhibit a selectivity that increases by from 40% to about 80% over an increase in permeability of from about 320% to about 350%.

As one example, a membrane may exhibit a selectivity increase of about 100% (expressed as $P_{penetrant\ A}/P_{penetrant\ B}$) over a 5% increase in permeability expressed as ln $(P_{penetrant\ A} \times 10^8, cm^2 min^{-1})$. As another example, a membrane may exhibit a selectivity increase of about 80% (expressed as $P_{penetrant\ A}/P_{penetrant\ B}$) over a 250% increase in permeability expressed as ln $(P_{penetrant\ A} \times 10^8, cm^2 min^{-1})$.

A non-limiting illustration of this is shown in FIG. 12, with particular reference to Regime I in that figure. As shown in the figure, the disclosed compositions exhibited—in one illustrative experiment—a selectivity that increased by about 50% over an increase of about 170% (calculated based on the units shown in x-axis of the figure) in permeability for the 0.66 chains/nm$^2$ samples.

The use of interstitial defects and interfacial tension in self-assembled polymer systems may be used to control material properties. Thus, manipulation of the polymer graft characteristics (e.g., molecular weight, grafting density) may affect the polymer chain free energy, changing both the self-assembly characteristics and transport capabilities of a mixed matrix membrane.

Illustrative Results Summary

A QCM was used to measure permeability and selectivity of neat PMA and PMA-grafted silica. Modest molecular weight grafts increased permeability and selectivity above that of the neat polymer, contrary to the conventional wisdom of Maxwell's prediction. Increased grafting density resulted in a large increase in permeability but a lesser increase in selectivity.

One non-limiting explanation for the increase is the presence of polymer-lean interstitial spaces in ordered (i.e., high graft density) samples into which polymers stretch to minimize the interphase energy that is relieved upon penetrant uptake and creates an additional energetic driving force. One may control this driving force by manipulating the polymer chain length and graft density, effectively altering the polymer/void interphase and maximizing the energetic gain from these systems. This allows for tunable transport properties that are easily altered for specific processes, resulting in increased permeability and selectivity of membrane systems and making them an alternative to existing separations technologies.

EXEMPLARY INDUSTRIAL APPLICATIONS

The disclosed technology is applicable in a broad range of applications. One such application is natural gas filtration. More specifically, grafted nanoparticle membranes in a natural gas purification system may be used to filter incoming material. Crude natural gas contains large amounts of carbon dioxide and hydrogen sulfide, both of which are hazardous to equipment and human health.

A filtration column using the disclosed materials may remove these species so that the effluent gas is lean in carbon dioxide and hydrogen sulfide. Syngas may also be cleaned using the same process. Typically, these membrane units are long tubes filled with many, many very small hollow fibers. Unpurified gas flows outside the membranes and the desired compound to remove passes through into the inside of the fibers.

As one non-limiting embodiment, one composition suitable for natural gas filtration is a polyacetylene such as poly(1-trimethylsilyl-1-propyne) (PTMSP) at moderate graft densities (0.3-0.5 chain/nm2) and molecular weights (60,000-70,000) with amine end groups grafted to 30 nm $TiO_2$ particles to remove carbon dioxide from crude natural gas. Other thermally-suitable polymers are useful.

The disclosed technology may also be used in air separations to selectively allow oxygen to permeate, which oxygen is then collected for optical and medical purposes. The reverse approach is also useful, i.e., using a material that prevents oxygen from permeating. This approach has utility in, e.g., food preservation.

It should be understood that the disclosed technology is not limited to gas-phase applications, as the disclosed technology may be applied to liquid applications as well. Membranes may be supported on a polymer membrane scaffold, which scaffold may itself be inert. As one example, an existing polymer membrane for a specific process could be coated with a composition according to the present disclosure. This may be accomplished by, e.g., dip coating, spin or spray casting, and like methods. The existing membrane would then support the graft-nanoparticle membrane layer. The graft-nanoparticle layer may be, e.g., in the sub-micron range.

What is claimed:

1. A system, comprising:
a chamber having an inlet,
the inlet in fluid communication with a first membrane,
the first membrane being configured to receive a material from the inlet and effect at least partial separation of a component of the material,
the first membrane comprising a plurality of graft nanoparticles,
a graft nanoparticle comprising a nanoparticle (a) having an average cross-sectional dimension in the range of from about 1 nm to about 50 nm and (b) having a population of polymer chains attached thereto, and
the plurality of graft nanoparticles being arranged in a periodic lattice structure.

2. The system of claim 1, further comprising a source of fluid in fluid communication with the inlet, the fluid comprising at least two components, one of the at least two components of the fluid being preferentially passed through the first membrane as compared to another of the at least two components.

3. The system of claim 1, wherein the first membrane is configured so as to preferentially pass natural gas therethrough.

4. The system of claim 1, further comprising a second membrane.

5. The system of claim 4, wherein, under the same conditions, the rate at which the first membrane passes a component therethrough is within about 10% of the rate at which the second membrane passes that same component.

* * * * *